(12) United States Patent
Ikeda (10) Patent No.: US 7,594,981 B2
(45) Date of Patent: Sep. 29, 2009

(54) METHOD FOR CONCENTRATING WATER-SOLUBLE ORGANIC MATERIAL

(75) Inventor: Shiro Ikeda, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 576 days.

(21) Appl. No.: 10/546,686

(22) PCT Filed: Feb. 20, 2004

(86) PCT No.: PCT/JP2004/001966

§ 371 (c)(1),
(2), (4) Date: Aug. 22, 2005

(87) PCT Pub. No.: WO2004/073841

PCT Pub. Date: Sep. 2, 2004

(65) Prior Publication Data

US 2006/0070867 A1    Apr. 6, 2006

(30) Foreign Application Priority Data

Feb. 21, 2003   (JP) .............................. 2003-044711

(51) Int. Cl.
*B01D 3/00* (2006.01)
*B01D 61/36* (2006.01)
*B01D 71/02* (2006.01)
*C07C 29/80* (2006.01)
*C07C 27/28* (2006.01)

(52) U.S. Cl. ............................ 203/18; 203/19; 203/25; 203/27; 203/41; 210/640; 568/913

(58) Field of Classification Search .................... 203/18, 203/19, 25, 27, 41, 91–98, DIG. 8; 210/640; 568/913, 916, 917
See application file for complete search history.

(56) References Cited

U.S. PATENT DOCUMENTS

| 3,303,105 | A | * | 2/1967 | Konikoff et al. ............... 203/11 |
| 4,405,409 | A |   | 9/1983 | Tusel et al. |
| 4,911,845 | A | * | 3/1990 | Hashimoto et al. .......... 210/640 |
| 4,952,751 | A | * | 8/1990 | Blume et al. ................. 585/818 |
| 4,953,694 | A | * | 9/1990 | Hayashi et al. .............. 202/180 |

(Continued)

FOREIGN PATENT DOCUMENTS

| DE | 44 30 148 A1 | 5/1996 |
| JP | 63-258601 A | 10/1988 |
| JP | 63-258602 A | 10/1988 |
| JP | 4-63110 A | 2/1992 |
| JP | 5-255154 A | 10/1993 |

(Continued)

OTHER PUBLICATIONS

Rautenbach R et al.: "Aufbereitung Azeotroper Stoffgemische" Chemietechnik, Huthig, Heidelberg, DE, vol. 25, No. 1 Jan. 1996, pp. 50-53, XP000554250.

(Continued)

*Primary Examiner*—Virginia Manoharan
(74) *Attorney, Agent, or Firm*—Sughrue Mion, PLLC (57) ABSTRACT

A method for concentrating a water-soluble organic material wherein a mixture of the water-soluble organic material with water is distilled in a distillation column (11), and the fraction from the top (11a) of the distillation column (11) is separated by the use of a membrane separator (14) into a permeated vapor ($F_2$) and a non-permeated vapor ($F_3$), which comprises once condensing the fraction to form a condensate, heating the condensate in an evaporator (13) to generate a vapor ($F_1$) having a pressure higher than the operation pressure for the distillation column (11), and introducing the vapor ($F_1$) to the membrane separator (14), thereby separating water from the mixture.

9 Claims, 5 Drawing Sheets

U.S. PATENT DOCUMENTS

| | | | |
|---|---|---|---|
| 5,013,447 A | | 5/1991 | Lee et al. |
| 5,028,298 A | * | 7/1991 | Baba et al. ............... 159/31 |
| 5,105,029 A | | 4/1992 | Nonimiya et al. |
| 5,427,687 A | * | 6/1995 | Blum et al. ............... 210/638 |
| 6,210,464 B1 | * | 4/2001 | Nakanishi et al. ............ 95/52 |
| 6,755,975 B2 | * | 6/2004 | Vane et al. ............... 210/640 |
| 2008/0210540 A1 | * | 9/2008 | Dieterle ..................... 203/19 |
| 2009/0004713 A1 | * | 1/2009 | Wynn et al. ............... 435/161 |
| 2009/0057128 A1 | * | 3/2009 | Vane et al. ................. 203/17 |

FOREIGN PATENT DOCUMENTS

| | | |
|---|---|---|
| JP | 7-227517 A | 8/1995 |
| JP | 9-71481 A | 3/1997 |
| JP | 2000-42386 A | 2/2000 |
| WO | WO 99/45035 A1 | 9/1999 |
| WO | WO 03/035222 A1 | 5/2003 |

OTHER PUBLICATIONS

Huang, "Pervaporation Membrane Separation Processes", Membrane Science Technology Series, 1, 1991, pp. 509-534, Elsevier Science Publishing Company, Amsterdam, Netherlands.

Sander et al. "Industrial Application of Vapour Permeation", Journal of Membrane Science, 61 (1991), pp. 113-129, Elsevier Science Publishers B.V., Amsterdam, Netherlands.

Martin et al., "Separating Azeotropic Mixtures", Sulzer Technical Review, Issue 3, 1998, pp. 12-15.

Maus, "Separation of methanol from methylesters by vapour permeation: experiences of industrial applications", Desalination, 148, 2002, pp. 315-319, Elsevier Science B.V.

"IPA Reprocessor", 1999, Kanto Chemical Co., Inc., Tokyo, Japan.

"Membrane Systems Pervaporation and Vapor Permeation", 2001, Sulzer Chemtech.

Fahmy et al., "Design Methodology for the Optimization of Membrane Separation Properties for Hybrid Vapor Permeation-Distillation Processes", Separation Science and Technology, 36(15), 2001, pp. 3287-3304, Marcel Dekker, Inc.

Jansen et al., "Methods to improve flux during alcohol/water azeotrope separation by vapor/permeation", Journal of Membrane Science, 68, 1992, pp. 229-239, Elsevier Science Publishers B.V., Amsterdam, Netherlands.

Van Veen, "Reduction of Energy Consumption in the Process Industry By Pervaporation with Inorganic Membranes: Techno-Economical Feasibility Study", ECN-C-01-073, Jul. 2001, pp. 1-29.

* cited by examiner

FIG. 5
- CONVENTIONAL -

FIG. 6
- CONVENTIONAL -

METHOD FOR CONCENTRATING WATER-SOLUBLE ORGANIC MATERIAL

TECHNICAL FIELD

The present invention is directed to a method for concentrating water-soluble organic materials, more specifically, a method for concentrating water-soluble organic materials with approximate 1.0 of relative volatility to water by the use of both distillation and membrane separation.

BACKGROUND ART

Regarding a method for concentrating a solution of a water-soluble organic material, the method for concentrating by the use of both distillation and membrane separation, that is, the use of both distillation column, and pervaporation membranes (hereinafter called PV membranes) or vapor permeation membranes (hereinafter called VP membranes) have been applied. Such method for concentrating by the use of such membranes is called pervaporation method (hereinafter called PV method), or vapor permeation method (hereinafter called VP method). In PV method, water permeates through a membrane due to the driving force generated by the difference between the vapor pressure of the water occurred in the solution according to the composition and the temperature of the supplied solution and the pressure of the vapor permeated through the membrane. In VP method, the water permeates through the membrane due to the driving force generated by the difference between the partial pressure of the water in the supplied vapor, and the pressure of the vapor permeated through the membrane. In either method, generally, pressures are reduced on the side of the permeated vapor through the membrane.

Figure 5:
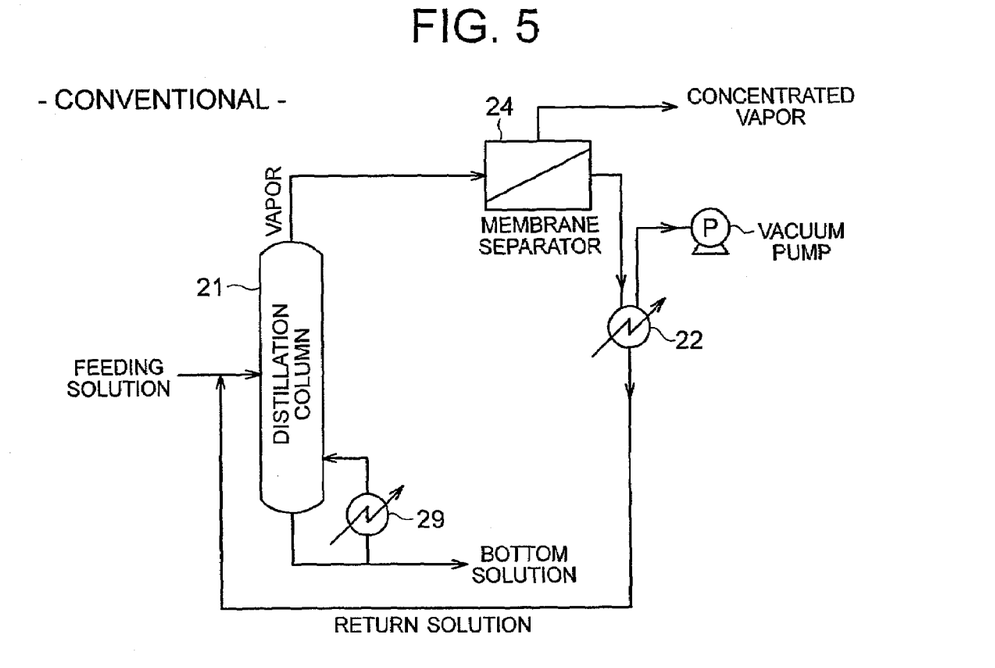
FIG. 5 is a block-diagram showing an example of the conventional method for concentrating the water-soluble organic material.

FIG. 5 shows a concentrating apparatus for water-soluble organic materials by the use of both distillation column and membrane separator. The concentrating apparatus is composed of distillation column 21, membrane separator 24 for separating water from the mixture of water with water-soluble organic material which is distilled by distillation column 21, condenser 22 for cooling the permeated vapor which has permeated through the membrane of membrane separator 24, and vacuum pump P for reducing the pressure on the side of the vapor permeated through the membrane. The solution at the bottom of distillation column 21 is heated by reboiler 29. For example, in the event of separating the ethanol solution in this apparatus, the vapor highly-containing ethanol is distilled from the top of distillation column 21, as the ethanol solution is fed to distillation column 21. As the distilled vapor is delivered to membrane separator 24, the water contained by the mixture permeates selectively through the membrane, and the concentrated ethanol is flown out of the outlet. The vapor permeated through the membrane is condensed by condenser 22, and returned to distillation column 21.

Figure 6:
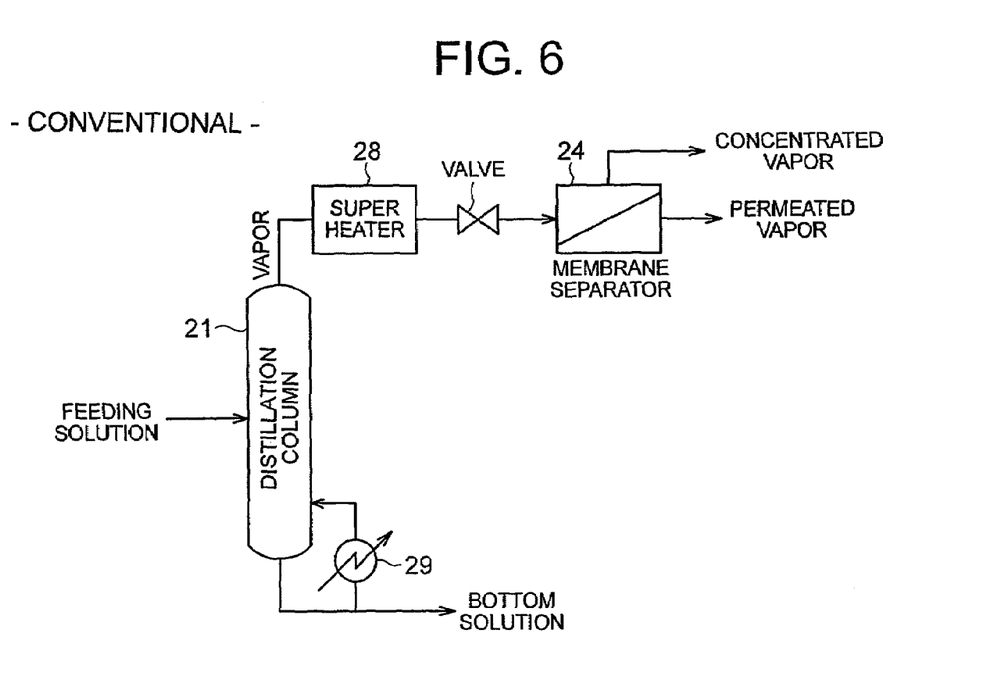
FIG. 6 is a block-diagram showing another example of the conventional method for concentrating the water-soluble organic material.

In Japan Patent Application Kokai Publication No. S63-258602, a method is disclosed for separating the volatile mixture into the permeated portion and non-permeated portion by feeding the evaporator with said volatile mixture, delivering the mixed vapor which is flown out of the top of said evaporator to the one side of the gas permeation membrane, and keeping the pressure lower on the other side of said gas permeation membrane. In this method, the evaporator can be one comprising trays, that is, a distillation column, and the temperature of the mixed vapor which is flown out of the top of the evaporator can be raised by a heater. The solution of the water-soluble organic material can be concentrated by means of such method by feeding the aqueous solution of the water-soluble organic material as the volatile mixture. FIG. 6 shows the concentrating apparatus comprising distillation column 21 and heater 28. As the separating apparatus shown in FIG. 6 is almost the same as the one shown in FIG. 5, except for comprising heater 28 and valve between distillation column 21 and membrane separator 24, only differences are described as follows. The vapor distilled from the top of distillation column 21 is heated up to the desirable temperature by heater 28 prior to being delivered to membrane separator 24. The vapor permeated through membrane separator 24 is flown out of the outlet on the permeated side.

According to this method, the pressure of the vapor delivered to membrane separator 24 is never higher than the operation pressure for distillation column 21, because the pressure of the vapor delivered to membrane separator 24 cannot be increased by heater 28 while it can raise the temperature of the vapor. Therefore, the operating pressure must be increased by raising the temperature at the bottom of distillation column 21 by means of adjusting the heat source for reboiler 29 in order to have a larger driving force of the water to permeate through the membrane of membrane separator 24 by increasing the pressure of the vapor delivered to membrane separator 24. Increase of operating pressures of distillation column causes the following problems: a) construction cost will increase because distillation column 21 requires resistance to higher pressures, 2) the distilling energy cost will increase because the heat source of higher temperature is required for evaporating the high boiling point component at the bottom of distillation column 21, c) the separation efficiency of distillation will decrease because the relative volatility of the water-soluble organic material to the water gets closer to 1.0.

OBJECT OF THE INVENTION

Therefore, the main object of the present invention is to provide a method for concentrating a water-soluble organic material by the use of distillation and membrane separation, wherein the driving force of the membrane separator is increased to gain higher permeation rate of the vapor through the membrane without increasing the operation pressure for the distillation column, at the same time saving the energy consumption.

DISCLOSURE OF THE INVENTION

As a result of the extensive study in the light of said purpose, the present inventors have discovered that a method for concentrating a water-soluble organic material by the use of a distillation and a membrane separator, wherein once condensing the fraction from the top or concentration section of the distillation column to form a condensate, evaporating it in the evaporator at a temperature of the same grade as the temperature of the solution at the bottom of the distillation column and feeding the vapor to the membrane separator, results is the increase in the permeation rate of the vapor through the membrane of the membrane separator because the pressure of the evaporated vapor is higher than the operating pressure of the distillation column due to lighter composition of the condensate fed to the vaporizer, and this discovery has brought them to the present invention.

More specifically, a method for concentrating a water-soluble organic material according to the present invention, wherein a water-soluble organic material is concentrated by distilling a mixture of the water-soluble organic material and water through a distillation column, introducing the fraction from the top or concentration section of the distillation column to a membrane separator, and separating the water from the mixture by the membrane separator, is characterized by getting condensate by condensing said mixture, generating vapor having a pressure higher than the operation pressure for the distillation column, and introducing the obtained vapor to the membrane separator.

Moreover, it is desirable to make the temperature to evaporate the fraction from the top or concentration section of the distillation column higher than the temperature at the bottom of the distillation column, and at least either the vapor permeated through the membrane of the membrane separator or the vapor which doesn't permeate the membrane is utilized as a heating source and/or stripping stream of the distillation column. It is also desirable to have 10-90% by mass of the condensed solution of the fraction from the top or concentration section of the distillation returned to the distillation column as a reflux, and the rest heated and pressurized. It is further desirable to have a solution fed by the distillation column heated by the heat of condensation of the fraction from the top or concentration section of the distillation column.

Preferably, the operation pressure for the distillation column is 50-150 kPa, and the membrane of the membrane separator is made from inorganic material, more preferably, from zeolite.

Preferably, the water-soluble organic material includes, but not limited to, alcohol, more preferably, ethanol or i-propyl alcohol.

EMBODIMENTS OF THE INVENTION

Figure 1:
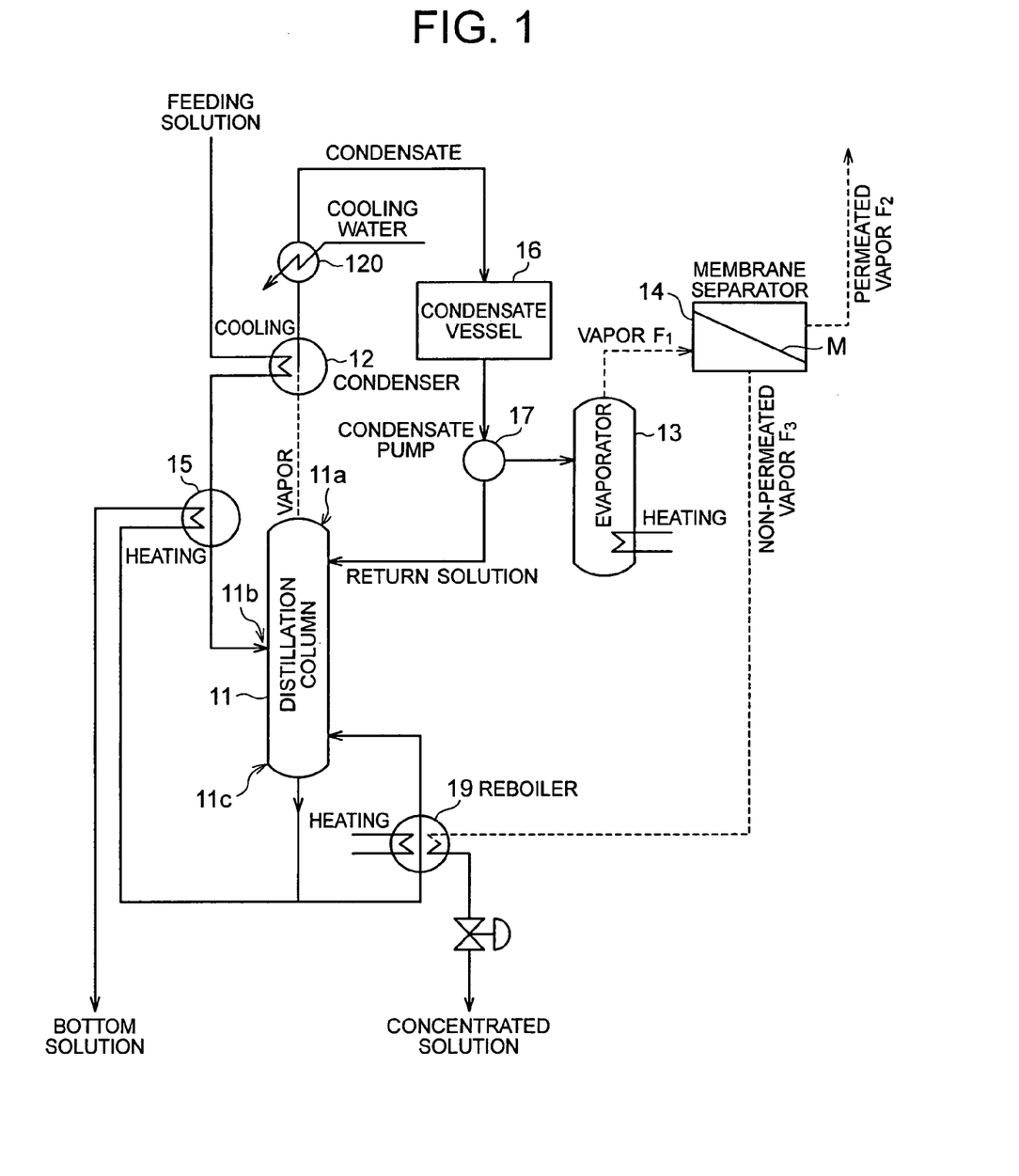
FIG. 1 is a block-diagram showing an example of the method for concentrating the water-soluble organic material according to the present invention.
Figure 4:
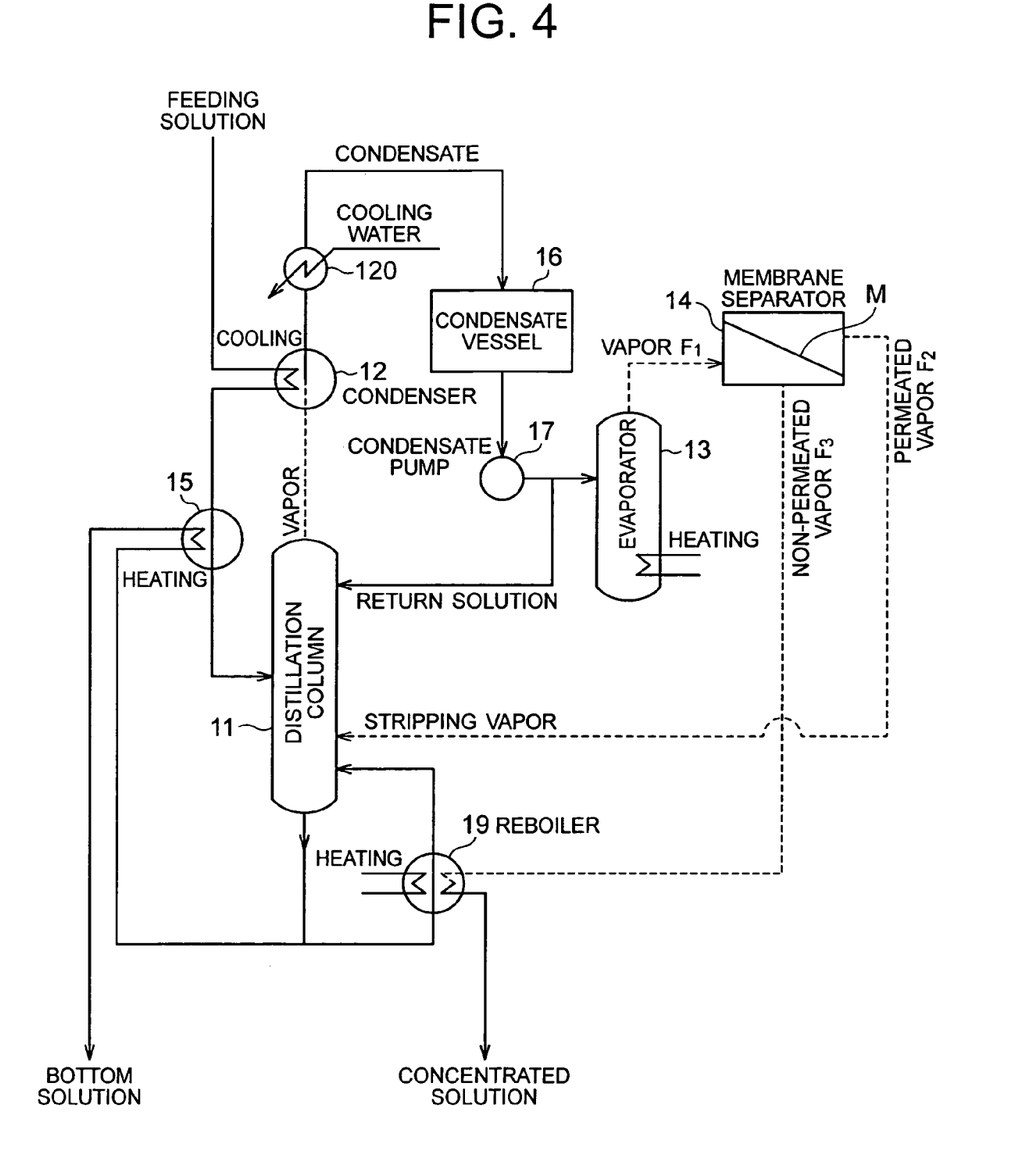
FIG. 4 is a block-diagram showing another example of the method for concentrating the water-soluble organic material according to the present invention.

The present invention is described by the following embodiment of the method for concentrating 10% by mass of ethanol solution, applying an apparatus, as shown in FIG. 1, but not limited to it. In FIG. 1 and FIG. 4, regarding the channels connecting each component composing the concentrating apparatus, the channels indicated in full line are ones for the liquid, and the channels indicated in dashed line are ones for vapor.

The concentrating apparatus shown in FIG. 1 comprises distillation column 11, condenser 12 for condensing the vapor from the top 11a of distillation column 11, evaporator 13 for evaporating the condensate from condenser 12, membrane separator 14 for separating the vapor from evaporator 13.

A type of distillation column 11 can be any type that is suitable for the distilling operation, including tray type and packed column-type, but not limited to. The middle section of distillation column 11 includes feeding part 11b for feeding the ethanol solution. A part of the solution at the bottom 11c is heated by reboiler 19 to form vapor that ascends in the column with exchanging heat and substances with the solution flowing down in the column. Therefore, the main constituent of the vapor is water at the bottom 11c, but the concentration of the ethanol contained by the vapor is higher at the vicinity of the top 11a of the column. The vapor from the top 11a of the column is delivered to condenser 12. The vapor can be flown out of the concentration section of the distillation column.

The rest of the solution from the bottom 11c is applied for the heat source of feed heater 15, and then is discharged as the bottom solution. The desirable operation pressure for distillation column 11 is 50-150 kPa. Over 150 kPa of operation pressure causes the following problems; a) fabrication cost of distillation column 11 becomes higher, b) energy cost becomes higher by increasing the temperature of the bottom 11c of the column, c) the relative volatility of ethanol to water is closer to 1.0. In the case of operation at pressures of less than 50 kPa, the condensation temperature of the vapor from the top 11a of the column is lower, and the temperature difference between the vapor and the cooling water is smaller, thereby the heat transfer area of condenser increases. Reboiler 19 heats the solution at the bottom of distillation column 11 by mainly the heat of condensation of non-permeated vapor F3 which is separated by membrane separator 14, and the heat of condensation of the steam supplied from outside.

Condenser 12 takes the heat out of the vapor from the top 11a of the column to form the condensate, which is pooled in condensate vessel 16. Apart of the pooled condensate is refluxed to the top 11a of the column by condensate pump, and the rest is delivered to evaporator 13. The constituent of the vapor that is not condensed by heating the feeding solution are condensed by the cooling water through auxiliary condenser 120. Preferably, the feeding solution is preheated up to approximately the boiling point by the heat of condensation of condenser 12, and by the feed heater.

Evaporator 13 generates vapor $F_1$ from the condensate that is delivered by condensate pump 17 by means of steam heating to deliver it to the inlet of membrane separator 14. As the water contained in the vapor $F_1$ of ethanol and water mixture $F_1$ permeates through membrane M selectively, permeated vapor $F_2$ is rich in water (e.g. ethanol 2% by mass) and non-permeated vapor $F_3$ is rich in ethanol (e.g. 99.5% by mass). The flow of the solution obtained by condensing non-permeated vapor $F_3$ is controlled in order to keep the feeding vapor $F_1$ and non-permeated vapor $F_3$ being pressurized. The partial pressure of the water contained in the feed vapor increases by feeding membrane separator 14 with high-pressure vapor $F_1$, thereby the permeation rate of the vapor $F_2$ increases. The pressure at the inside of evaporator 13 is controlled so that the evaporation temperature at the inside of evaporator 13 is kept 5-10 degrees C. higher than the temperature at the bottom 11c of distillation column, thereby non-permeated vapor $F_3$ can be applied for heating reboiler 19.

Figure 2:
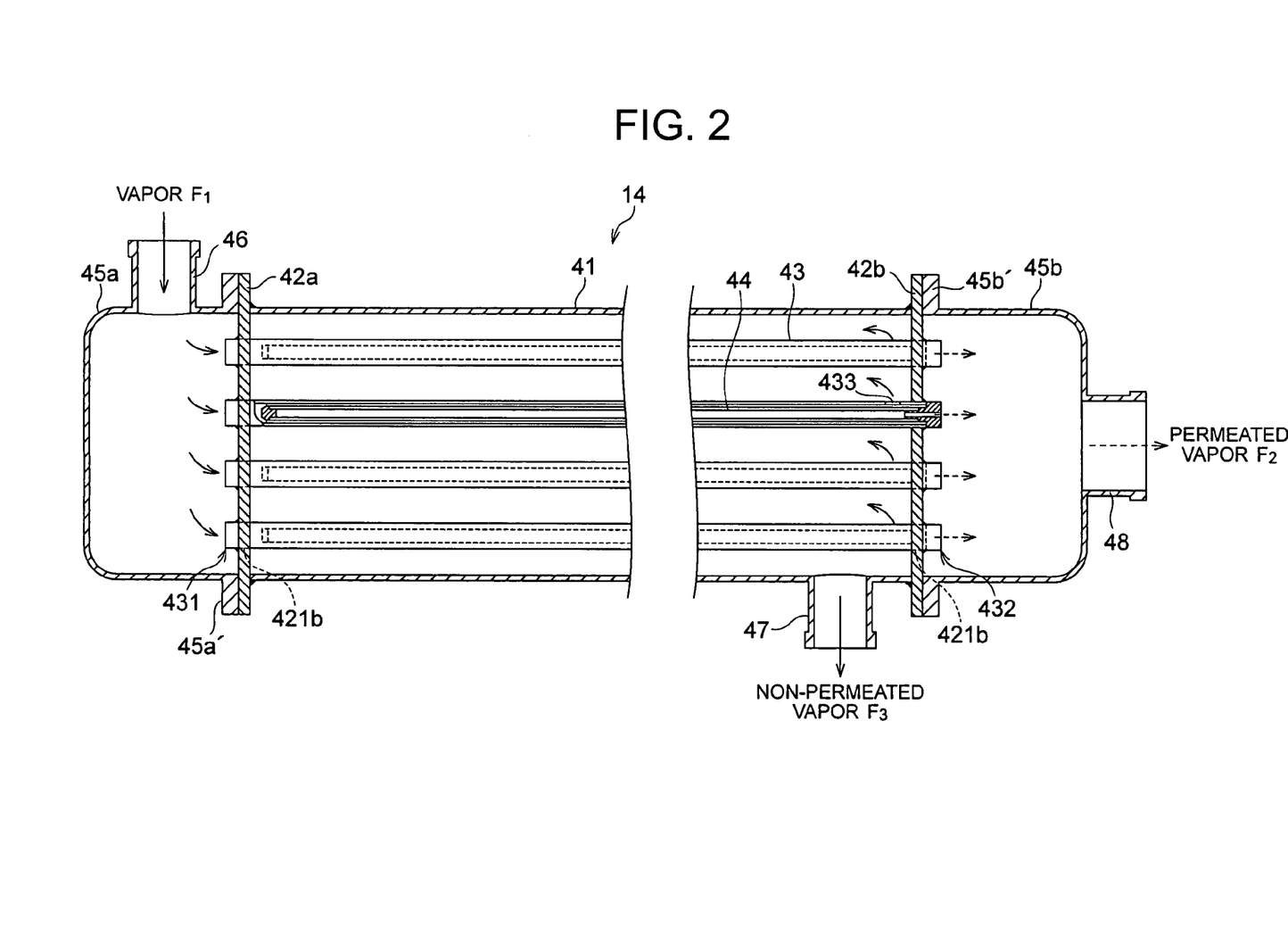
FIG. 2 is a cross-sectional view showing an example of the membrane separator.

A desirable type of membrane separator 14 is a shell-and-tube type of module comprising a tubular membrane element composed of a porous material of tubular support on which a membrane is formed. FIG. 2 shows an example of membrane separator 14 which can be applied for concentrating method according to the present invention. This membrane separator 14 comprises cylindrical shell 41, supporting plates 42a and 42b fixed at the both ends of shell 41, a plural of outer tubes extending at the long side of shell 41 and supported by supporting plates 42a and 42b, tubular membrane element 44 attached to the inside of the long side of outer tube 43, hoods 45a and 45b attached to shell 41 covering upon supporting plates 42a and 42b. Inlet 46 for vapor $F_1$ projects from hood 45a, and outlet 47 for non-permeated vapor $F_3$ projects outward from shell 41. Vapor outlet 47 is attached at the vicinity of supporting plate 42b. Outlet 48 for permeated vapor $F_2$ is attached to hood 45b'. Flanges 45a' and 45b' of hoods 45a and 45b are engaging tightly with supporting plates 42a and 42b respectively.

Each supporting plates 42a and 42b includes a plural open mouths 421a and 421b which are placed at the long side of shell 41, exactly facing to each other. Head end 431 of outer tube 43 fixed at open mouth 421a, and tail end 432 of said outer tube 43 is engaged with open mouth 421b facing to open mouth 421a, thereby each outer tube 43 is carried by supporting plates 42a and 42b. Vapor through trap 433 is formed at each outer tube 43 at the vicinity of supporting plate 42b.

Figure 3:
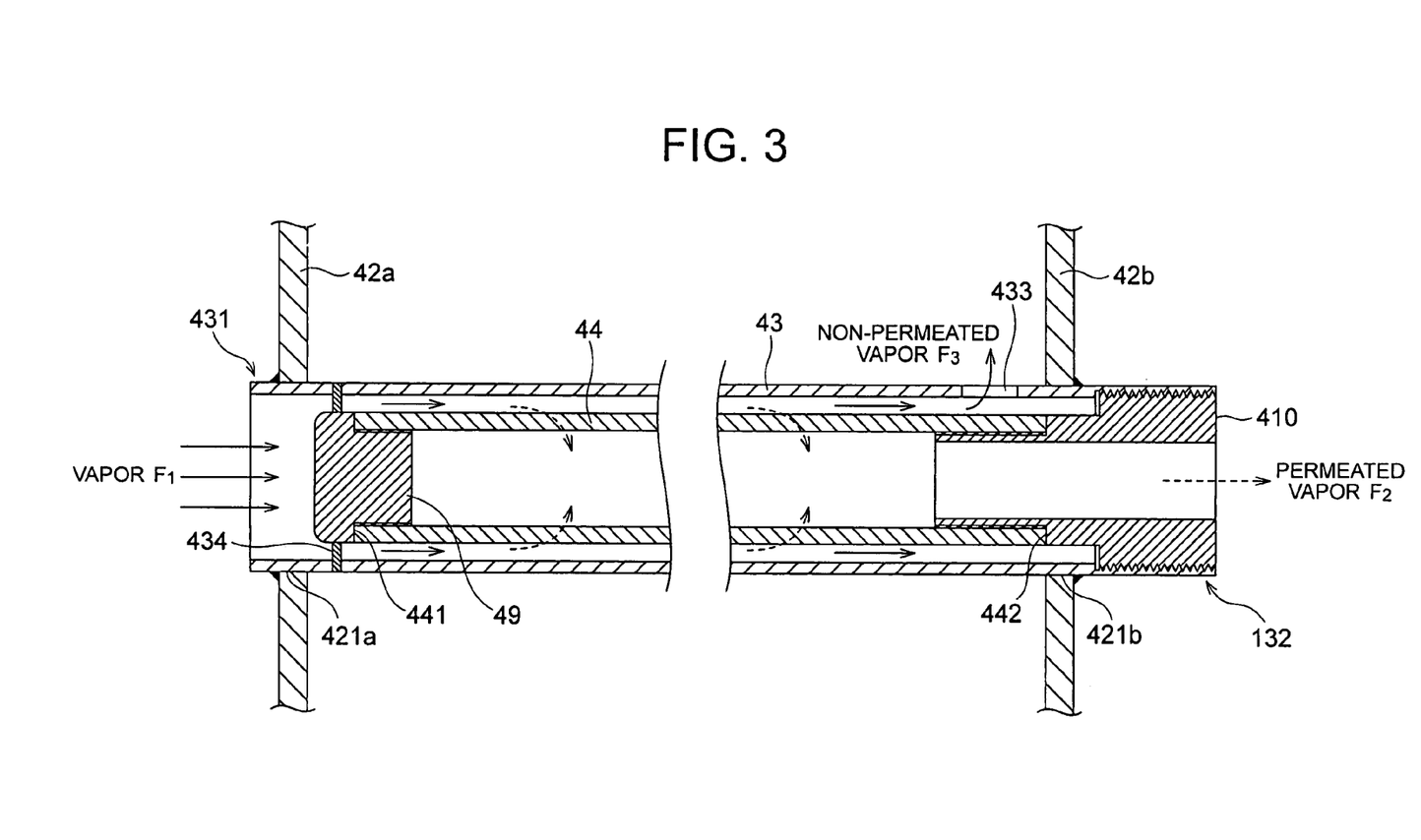
FIG. 3 is an enlarged cross-sectional view showing a tubular membrane element and outer tube of the membrane separator.

FIG. 3 shows the detailed structure of outer tube 43 and tubular membrane element 44 which are carried by supporting plates 42a and 42b. The head end (the side of hood 45a) of tubular membrane element 44 is sealed end 441, and the tail end (the side of hood 45b) is open end 442. Sealed end 441 is sealed with sealing material 49. Open end 442 is engaging with supporting material 410 that is screwed together with tail end 432 of outer tube 43. Outer tube 43 includes a plural of pin parts 434, which are projecting from the inside of outer tube 43, in the vicinity of supporting plates 42a. The head tail of pin part 434 is carrying tubular membrane element 44 by means of connecting directly to sealing material 49.

As shown in FIG. 2 and FIG. 3, in the event of feeding shell 41 with vapor $F_1$ through vapor inlet 46, vapor $F_2$ permeates tubular membrane element 44, and flows out for permeated-vapor outlet 48. Vapor $F_3$ (non-permeated vapor) that doesn't permeate through tubular membrane element 44 runs through the gap between outer tube 43 and tubular membrane element 44, and flows out of vapor through trap 433. And then non-permeated vapor $F_3$ runs through the outside of outer tube 43, and flows out of vapor outlet 47.

Vapor $F_1$ with higher pressure than the operation pressure for distillation column, which is generated by evaporating the condensate through evaporator at the temperature 5-10 degrees C. higher than one at the bottom 11c of distillation column, is delivered to membrane separator 14, thereby the driving force to permeate through the membrane M (tubular membrane element 44) increases, and thus the permeating rate of the vapor $F_2$ increases. Moreover, this makes it possible to heat reboiler 19 of distillation column 11 with non-permeated vapor $F_3$ that doesn't permeate through membrane M of membrane separator 14. In order to have a larger driving force for permeation through membrane M, the pressure on the side of permeated vapor $F_2$ can be reduced by means of installing a condenser and/or a vacuum pump on that side. Ethanol content of permeated vapor $F_2$ is 0.5-5% by mass, non-permeated vapor $F_3$ is 99-99.7% by mass. Non-permeated vapor $F_3$ is condensed into the condensate thereby heat of condensation is utilized as a heating source of reboiler 19. Flow of the condensate to discharge is controlled to keep high pressure is the vapor $F_1$ and non-permeated vapor $F_3$.

The concentrating apparatus shown in FIG. 4 is primarily the same as one shown in FIG. 1, except for making permeated vapor $F_2$ a stripping vapor to distillation column 11, so that only the difference is described as follows. Preferably, the operation pressure for distillation column 11 is the section of atmospheric pressure (100 kPa). In the event of having 500 kPa of pressure of vapor $F_1$ at the inlet of membrane separator 14, and 0.6 of molar ratio of the ethanol contained by vapor $F_1$, the pressure of $F_2$ at the outlet is 150 kPa. Vapor $F_2$ stripping steam to distillation column 11 because vapor $F_2$ contains mostly water, and a little ethanol.

In the case where the operating pressure is less than atmospheric in the distillation column, the permeated vapor $F_2$ can be applicable as the stripping steam even if its pressure is less than atmospheric. It is also possible to apply permeated vapor $F_2$ for the heating source for reboiler 19, instead of making it stripping steam.

Membrane M comprised by membrane separator 14 is not specific, and can be made from such materials as a high-molecular weight polyvinyl alcohol (PVA) and polyimide, but is preferable to be made from such inorganic materials as zeolite and zirconia, more preferably, from zeolite. For example, such a membrane that is fabricated by forming thin zeolite film on a tubular support made of porous alumina is especially desirable. A type of such zeolite includes, but is not limited to, ZSM-5 type, A type, Y type which can be selected arbitrarily based on the type of the water-soluble organic material to be concentrated.

The water-soluble organic material which is concentrated by the method according to the present invention includes, but is not limited to, ethanol, methanol, i-propyl alcohol, acetone, dioxane, DMF, and preferably, alcohol, more preferably, ethanol or i-propyl alcohol. Preferably, the mixture of a water-soluble organic material and water is a solution, but not limited to.

The present invention is described in more detailed by the following embodiments, but not limited to them.

Embodiment 1

10% by mass of the ethanol solution was concentrated by means of the concentrating apparatus shown in FIG. 1. The ethanol solution preheated up to 90 degrees C. was fed to distillation column 11 at the rate of 100 kg/h. The heat of condensation of the vapor from the top 11a of the column and a part of the heat recovered from the solution discharged from the bottom of the column applied for pre-heating the feeding solution. The vapor of which ethanol content is 80% by mass was distilled from the top 11a of the column. The condensate that was obtained by condensing the vapor through condenser 12 was delivered to evaporator 13 at the rate of 12.4 kg/h, and the rest was returned to the top 11a of distillation column. The solution at the bottom of the column contains 100 ppm of ethanol.

Through evaporator 13 with 300 kPa of the inside pressure, the vapor of which ethanol content is 80% by mass was evaporated at the rate of 12.4 kg/h, and delivered to membrane separator 14. Membrane M of membrane separator 14 was composed of a A-type zeolite film which is formed on the tubular support made of the porous alumina. Permeated vapor $F_2$ containing 0.25% by mass of ethanol permeated through membrane M, and non-permeated vapor $F_3$ containing 99.5% by mass of ethanol was flown out. The temperature at the bottom 11c of distillation column was 101 degrees C., and the evaporation temperature of evaporator 13 was 108 degrees C.

Non-permeated vapor $F_3$ was condensed, and 2,000 kcal/h of the condensation heat was applied for the heat source for reboiler 19. Besides heating reboiler 19 by the condensation heat of non-permeated vapor $F_3$, the solution at the bottom 11c of the column was heated by the steam with 7,000 kcal/h, and evaporator 13 was heated by the steam with 4,000 kcal/h.

FIELD OF THE INVENTION

As described above, by means of the method for concentrating a water-soluble organic material according to the present invention, wherein the condensate obtained by condensing the vapor discharged from the top or concentration section of the distillation column is evaporated to generate the vapor, and the obtained vapor is delivered into the membrane separator, the pressure of the vapor delivered into the membrane separator increases, thereby the driving force for permeating through the membrane increases, and thus the permeating rate of the vapor increases. Therefore, in this method, it is possible to concentrate the solution of the water-soluble organic material efficiently. Moreover, it is possible to keep the operation pressure for the distillation column low, and to save the consuming energy by applying the permeated vapor for the heat source at the bottom of the distillation column.

The invention claimed is:

1. A method for concentrating a water-soluble organic material comprising:
   distilling a mixture of the water-soluble organic material with water in a distillation column,
   condensing a fraction from a top section of said distillation column into a condensate,
   returning a part of said condensate to said distillation column via a pump and introducing the rest of said condensate to an evaporator via said pump,
   heating the rest of said condensate within said evaporator to generate a vapor mixture with a higher pressure than an operating pressure of said distillation column,
   introducing said vapor mixture with the higher pressure to a membrane separator, and
   separating said vapor mixture into a non-permeated vapor and a permeated vapor that is rich in water in said membrane separator.

2. A method for concentrating a water-soluble organic material according to claim 1, wherein a vapor permeated through the membrane of said membrane separator is utilized as a stripping steam for said distillation column.

3. A method for concentrating a water-soluble organic material according to claim 1 or 2, wherein 10-90% of the condensate is returned to said distillation column, and the rest is introduced to said evaporator.

4. A method for concentrating a water-soluble organic material according claim 1, wherein a reboiler for said distillation column is heated by the use of the condensation heat of said non-permeated vapor.

5. A method for concentrating a water-soluble organic material according to claim 1, wherein the operation pressure for said distillation column is 50-150 kPa.

6. A method for concentrating a water-soluble organic material according claim 1, wherein a membrane of said membrane separator is made of inorganic material.

7. A method for concentrating a water-soluble organic material according to claim 6, wherein said inorganic material is zeolite.

8. A method for concentrating a water-soluble organic material according to claim 1, wherein said water-soluble organic material is alcohol.

9. A method for concentrating a water-soluble organic material according to claim 8, wherein said water-soluble organic material is ethanol or i-propyl alcohol.

* * * * *

(12) INTER PARTES REEXAMINATION CERTIFICATE (544th)
United States Patent
Ikeda (10) Number: US 7,594,981 C1
(45) Certificate Issued: Feb. 26, 2013

(54) METHOD FOR CONCENTRATING WATER-SOLUBLE ORGANIC MATERIAL

(75) Inventor: Shiro Ikeda, Tokyo (JP)

(73) Assignee: Mitsubishi Chemical Corporation, Minato-Ku, Tokyo (JP)

Reexamination Request:
No. 95/002,071, Aug. 8, 2012

Reexamination Certificate for:
Patent No.: 7,594,981
Issued: Sep. 29, 2009
Appl. No.: 10/546,686
Filed: Aug. 22, 2005

(21) Appl. No.: 95/002,071

(22) PCT Filed: Feb. 20, 2004

(86) PCT No.: PCT/JP2004/001966
§ 371 (c)(1),
(2), (4) Date: Aug. 22, 2005

(87) PCT Pub. No.: WO2004/073841
PCT Pub. Date: Sep. 2, 2004

(30) Foreign Application Priority Data

Feb. 21, 2003 (JP) .................. 2003-044711

(51) Int. Cl.
*B01D 3/00* (2006.01)
*B01D 61/36* (2006.01)
*B01D 71/02* (2006.01)
*B01D 3/14* (2006.01)
*C07C 29/80* (2006.01)
*C07C 27/28* (2006.01)

(52) U.S. Cl. ................ 203/18; 203/19; 203/25; 203/27; 203/41; 210/640

(58) Field of Classification Search ................ None
See application file for complete search history.

(56) References Cited

To view the complete listing of prior art documents cited during the proceeding for Reexamination Control Number 95/002,071, please refer to the USPTO's public Patent Application Information Retrieval (PAIR) system under the Display References tab.

*Primary Examiner* — Ling Xu (57) ABSTRACT

A method for concentrating a water-soluble organic material wherein a mixture of the water-soluble organic material with water is distilled in a distillation column (11), and the fraction from the top (11a) of the distillation column (11) is separated by the use of a membrane separator (14) into a permeated vapor ($F_2$) and a non-permeated vapor ($F_3$), which comprises once condensing the fraction to form a condensate, heating the condensate in an evaporator (13) to generate a vapor ($F_1$) having a pressure higher than the operation pressure for the distillation column (11), and introducing the vapor ($F_1$) to the membrane separator (14), thereby separating water from the mixture.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-9 are cancelled.

\* \* \* \* \*